United States Patent
Tampieri et al.

(10) Patent No.: US 9,326,948 B2
(45) Date of Patent: May 3, 2016

(54) IMPLANTS FOR "LOAD BEARING" BONE SUBSTITUTIONS HAVING HIERARCHICAL ORGANIZED ARCHITECTURE DERIVING FROM TRANSFORMATION OF VEGETAL STRUCTURES

(75) Inventors: Anna Tampieri, Faenza (IT); Simone Sprio, Bologna (IT); Andrea Ruffini, Bagnacavallo (IT); Julia Will, Obermichelbach (DE); Peter Greil, Weisendorf (DE); Frank Muller, Jena (DE); Julian Martinez Fernandez, Seville (ES); Carmen Torres Raya, Mairena del Aljarafe (ES); Francisco Manuel Varela Feria, Seville (ES); Joaquin Ramirez Rico, Tomares (ES); Marie-Francoise Harmand, Bordeaux (FR)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 139 days.

(21) Appl. No.: 13/884,123
(22) PCT Filed: Nov. 8, 2011
(86) PCT No.: PCT/IB2011/054980
§ 371 (c)(1),
(2), (4) Date: Dec. 28, 2013
(87) PCT Pub. No.: WO2012/063201
PCT Pub. Date: May 18, 2012

(65) Prior Publication Data
US 2014/0134258 A1  May 15, 2014

(30) Foreign Application Priority Data
Nov. 8, 2010 (IT) .............................. MI2010A2070

(51) Int. Cl.
A61F 2/28 (2006.01)
A61K 38/39 (2006.01)
(Continued)

(52) U.S. Cl.
CPC . *A61K 9/501* (2013.01); *A61F 2/28* (2013.01); *A61K 38/39* (2013.01); *A61L 27/10* (2013.01); *A61L 27/12* (2013.01); *A61L 27/46* (2013.01); *A61L 27/56* (2013.01); *A61L 2430/02* (2013.01)

(58) Field of Classification Search
CPC .......... A61F 2/28; A61K 38/39; A61K 9/501; A61L 2430/02; A61L 27/10; A61L 27/12; A61L 27/46; A61L 27/56
See application file for complete search history.

(56) References Cited

U.S. PATENT DOCUMENTS 5,522,894 A * 6/1996 Draenert .................... 623/23.61
2004/0013712 A1 1/2004 Parma
(Continued)

FOREIGN PATENT DOCUMENTS

EP 1447104 A1 8/2004
EP 1452488 A1 9/2004
(Continued)

OTHER PUBLICATIONS

Tempieri et al. (J Mater Chem 2009; 19:4973-4980).*
(Continued)

*Primary Examiner* — Ernst V Arnold
(74) *Attorney, Agent, or Firm* — Pearne & Gordon LLP

(57) ABSTRACT

The present invention relates to a bone substitute comprising a core based on hydroxyapatite (HA), obtained from at least one porous wood, or based on collagen fibers and hydroxyapatite, and a shell, based on hydroxyapatite (HA) or silicon carbide (SiC), obtained from at least one wood having a lower porosity than the at least one wood of the core. The porous wood has a total porosity of between 60% and 95%, preferably between 65% and 85%, and it is selected from amongst the choices of rattan, pine, abachi and balsa wood. The wood of the shell has a porosity of between 20% and 60%, preferably between 30% and 50%. The bone substitute is utilized for the substitution and regeneration of bone, preferably for bones subjected to mechanical loads, such as long bones of the leg and arm, preferably the tibia, metatarsus, femur, humerus or radius.

17 Claims, 14 Drawing Sheets

(51) Int. Cl.
  *A61L 27/10* (2006.01)
  *A61L 27/12* (2006.01)
  *A61L 27/46* (2006.01)
  *A61K 9/50* (2006.01)
  *A61L 27/56* (2006.01)

(56) References Cited

U.S. PATENT DOCUMENTS

2006/0292350 A1  12/2006  Kawamura et al.
2008/0262121 A1  10/2008  Landi et al.
2009/0232875 A1   9/2009  Tampieri et al.

FOREIGN PATENT DOCUMENTS

| ES | 2187371 | 6/2003 |
| WO | 0209790 A1 | 2/2002 |
| WO | 03031331 A1 | 4/2003 |
| WO | 2006092718 A2 | 9/2006 |
| WO | 2007045954 A1 | 4/2007 |

OTHER PUBLICATIONS

Narayan (Advances in Bioceramics and porous ceramics II; 2009;30(6); 2 pages).*
Carvallo et al. (European Cells and Materials 2004,7(suppl 2):58-59).*
Eichenseer, C., et al., "Biomorphous Porous Hydroxyapatite-Ceramics From Rattan (Calamus Rotang)", Journal of Materials Science: Materials in Medicine, Kluwer Academic Publishers, BO, Aug. 23, 2009, vol. 21, No. 1, pp. 131-137.
Tampieri, et al., "From Wood to Bone: Multi-Step Process to Convert Wood Hierarchical Structures Into Biomimetic Scaffolds for Bone Tissue Engineering", Journal of Materials Chemistry, Jun. 15, 2009, vol. 19, pp. 4973-4980.

* cited by examiner

Fig, 4

| Material | Strain (%) | Strength (GPa) |
|---|---|---|
| bioSiC AL00A | 11-16 | 1.6 ± 0.2* |
| bioSiC EN01A | 11-12 | 1.6 ± 0.1 |
| bioSiC QU02A | 7-9 | 1.0 ± 0.1 |

Fig. 5

A
B
Fig. 11

IMPLANTS FOR "LOAD BEARING" BONE SUBSTITUTIONS HAVING HIERARCHICAL ORGANIZED ARCHITECTURE DERIVING FROM TRANSFORMATION OF VEGETAL STRUCTURES

FIELD OF THE INVENTION

The present invention relates to a biomorphic bone substitute for the substitution and regeneration of portions of bone subjected to mechanical loads (load-bearing).

BACKGROUND ART

The social and economic impact of degenerative diseases affecting bone tissue makes it necessary to develop synthetic bone substitutes that are capable of exhibiting superior biofunctional properties, above all in orthopaedics, where surgical operations for bone reconstruction and regeneration are steadily increasing and increasingly involve young patients who are still active. In this regard, the biomechanical properties required of a bone substitute are particularly important, in order for it to promote the development and remodelling of new bone tissue under mechanical loads, minimizing recourse to fixation techniques, while at the same time being integrated and resorbed as much as possible by the newly forming bone tissue.

The remarkable and unsurpassable biomechanical properties of natural bone are strictly a consequence of its anisotropic morphology that is hierarchically organized in a range of scales from sub-micrometer to the macroscopic dimensions, so that the bone tissue is able to adapt continually to changes in the mechanical load. On the basis of these continual and varying stresses, the bone remodels itself by means of mechanisms in the cells that act as sensors of variations in the pressure of the extracellular fluid due to mechanical stimuli. Such mechanisms permit the removal of damaged bone and its substitution with new tissue having an organized, and thus fully functional morphology. This mechanism is of crucial importance for the survival of bone tissue subjected to mechanical loads and it can be activated only in the presence of a hierarchically organized structure.

As yet, an optimal solution for the replacement and regeneration of portions of bone subjected to mechanical loads (load-bearing) has not been found, as there are no known bone scaffolds that are both bioactive/bioresorbable and resistant to the mechanical loads to which certain bone portions of the body are subjected, such as the long bones of the leg or arm (for example the metatarsus, femur, tibia, humerus and radius).

This drawback is overcome by the present invention, which makes available a bone substitute for bone generation in general and in particular for the regeneration of portions of bone preferably subjected to mechanical loads (load-bearing) as outlined in the appended claims.

SUMMARY OF THE INVENTION

The bone substitute of the invention is provided with a morphology organized in a hierarchical manner in the three spatial dimensions. The bone substitute is obtained starting from vegetal structures that exhibit in themselves a hierarchically organized structure and a porosity range compatible with the requirements needed for a bone substitute, that is, a macroporosity capable of permitting cell colonization and proliferation and the formation of an appropriate vascularization tree, interconnected with a microporosity capable of permitting the exchange of nutrient fluids and those containing waste products of cell metabolism.

Such vegetal structures are transformed into inorganic bioactive/bioresorbable materials by means of suitable thermal and chemical processes, while maintaining their original structure and morphology. These devices, which by virtue of their nature are defined as biomorphic (that is, they reproduce in detail the structure of a natural material), intend to mimic the in vivo biomechanical behaviour of bone and owing to their chemical composition, which reproduces well that of natural bone, they are able to induce the same responses at the cellular level, guiding the formation, proliferation and maturation of new bone tissue.

At the same time, the bone substitute of the invention is able to exhibit a biomechanical behaviour such as to be able to be used for substitutions and regeneration of portions of bone subjected to mechanical loads (load-bearing), such as for example the long bones of the leg and arm. The bone substitute of the invention can also be utilized for the substitution and regeneration of portions of bone that are not subjected to mechanical loads. In fact, the substitute is adaptable to any regeneration need.

BRIEF DESCRIPTION OF THE DRAWINGS

The invention is described herein in detail also with reference to the appended figures, wherein:

FIG. 5 shows the compression strength of several SiC samples;

FIG. 11A shows a complete bone substitute according to the invention, in which the shell is in SiC and the core is collagen mineralized with hydroxyapatite substituted with carbonate and magnesium;

FIG. 11B shows a complete bone substitute according to the invention, in which the shell is in SiC and the core is biomorphic hydroxyapatite substituted with carbonate;

DETAILED DESCRIPTION OF THE INVENTION

Figure 1:
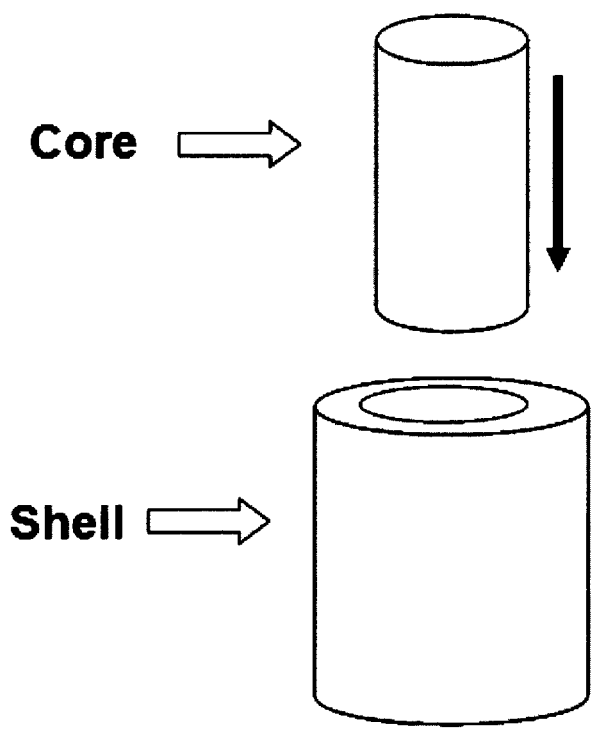
FIG. 1 is a schematic drawing of a particular embodiment of the biomorphic bone substitute of the invention.

The inventors of the present patent application have surprisingly found that by encapsulating a biomorphic scaffold based on hydroxyapatite (HA) obtained from a wood having high porosity (or a scaffold based on collagen fibres and hydroxyapatite) in a biomorphic shell based on hydroxyapatite (HA) or silicon carbide (SiC) obtained from a wood having reduced porosity, a bone substitute is obtained that has mechanical strength properties as well as the characteristics of bioactivity and/or bioresorbability. The bone substitute can thus be employed for the substitution and regeneration of bone portions subjected to mechanical loads (load-bearing), but also of bone portions not subjected to mechanical loads. Such portions of bone are the long bones of the leg and arm, for example the tibia, metatarsus, femur, humerus and radius.

Therefore, the bone substitute of the invention comprises a core, based on hydroxyapatite (HA), obtained from at least one porous wood (or based on collagen and hydroxyapatite) and a shell, based on hydroxyapatite (HA) or silicon carbide (SiC), obtained from at least one wood having a lower porosity than at least one wood of the core.

The wood utilized for the core can be defined as a wood having high porosity, where high porosity is intended as a total porosity of between 60% and 95%, preferably between 65% and 85%.

Preferably the wood having high porosity comprises an amount of wide pores that ranges between 35% and 70%, preferably between 40% and 65% of the total amount of pores. Such pores preferably have a diameter ranging between 70 and 400 µm, preferably between 80 and 300 µm. Examples of woods having high porosity are rattan, pine, abachi and balsa wood.

The wood utilized for the shell can be defined as a wood having reduced porosity, where reduced porosity is intended as a porosity of between 20% and 60%, preferably between 30% and 50%.

Examples of woods having reduced porosity are sipo, oak, rosewood and kempas.

The core based on collagen and hydroxyapatite preferably comprises collagen fibres mineralized with biomimetic hydroxyapatite. Hereinafter in this disclosure, biomimetic hydroxyapatite is intended as hydroxyapatite partially substituted with ions relevant for the stimulation of bone regeneration processes, preferably carbonate, magnesium, silicon and/or strontium, more preferably carbonate and magnesium or only carbonate ions.

The core deriving from wood structures having high porosity or from a structure of collagen mineralized with ionically substituted HA simulates the inner spongy part of the natural bone, while the shell deriving from woods having reduced porosity and high mechanical strength simulates the cortical part of the bone.

In an embodiment of the invention, the shell is coated with a thin layer based on hydroxyapatite (HA) and/or collagen, so as to increase cellular adhesion and proliferation, and thus osteointegration in the surrounding bone tissue.

Preferably, said layer comprises collagen mineralized with HA or HA substituted with ions relevant for the stimulation of bone regeneration processes, preferably carbonate, magnesium, silicon and/or strontium, more preferably carbonate (biomimetic HA) ions.

The hydroxyapatite-based core deriving from woods having high porosity preferably comprises hydroxyapatite partially substituted with ions relevant for the stimulation of bone regeneration processes, preferably carbonate, magnesium, silicon and/or strontium ions, more preferably carbonate ions, or a biphasic mixture comprising ionically substituted hydroxyapatite and β-tricalcium phosphate (beta-TCP; $Ca_3(PO_4)_2$). Alternatively, the core can comprise a hybrid compound comprising collagen mineralized with biomimetic hydroxyapatite.

The shell based on hydroxyapatite deriving from woods having reduced porosity preferably comprises biomimetic hydroxyapatite, or a biphasic mixture comprising biomimetic hydroxyapatite and β-tricalcium phosphate (beta-TCP; $Ca_3(PO_4)_2$). Alternatively, the shell deriving from woods having reduced porosity preferably comprises silicon carbide.

In a preferred embodiment, when a silicon carbide shell is utilized, such shell is coated with a bioactive layer of collagen mineralized with biomimetic hydroxyapatite or of biomimetic hydroxyapatite alone.

In fact, although silicon carbide is an inert, non-toxic material, at the same time it does not facilitate cellular adhesion and proliferation. Thus, the utilization of uncoated silicon carbide could slow down healing of the bone.

In another embodiment, such coating layer can also be applied in the case in which the shell comprises HA partially substituted with ions relevant for the stimulation of bone regeneration processes, or a biphasic mixture of HA and beta-TCP, to promote even more the reconstruction of natural bone. In this case, application of the coating is preferably carried out by means of SBF immersion (as described herein below). In fact, in this manner, one would obtain an enrichment of the shell with ions useful for bone regeneration.

Figure 2:
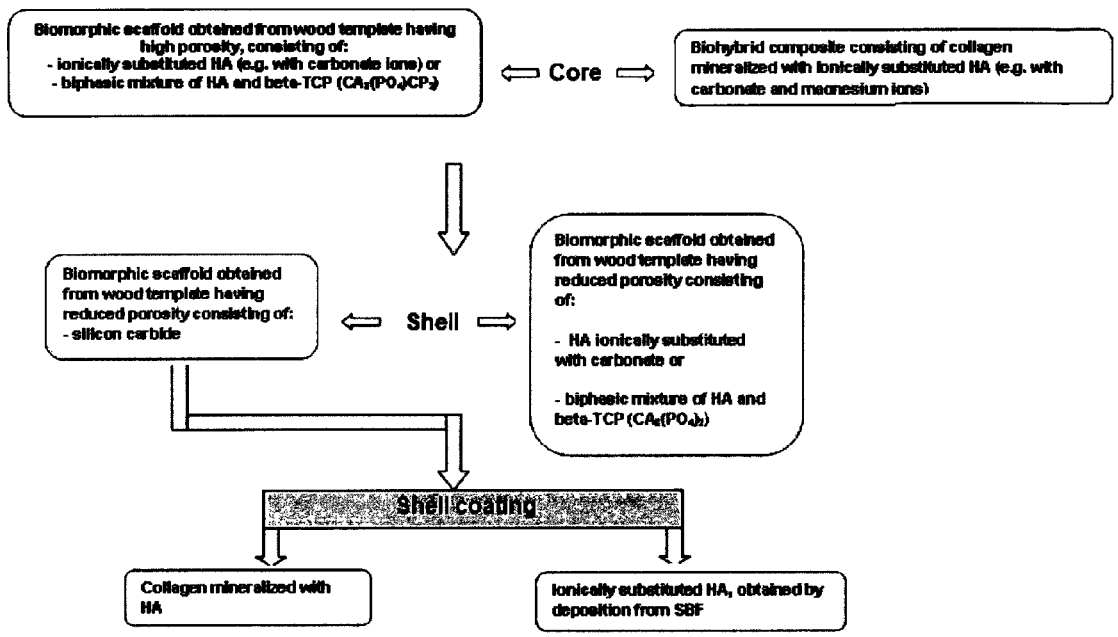
FIG. 2 is a block diagram that illustrates the possible embodiments of the biomorphic substitute of the invention.

The various shell typologies listed hereinabove can be matched with the various core typologies indicated above, according to the desired application, particularly according to the mechanical strength required. An outline of the various embodiments of the bone substitute of the invention is given in FIG. 2. For applications requiring high mechanical strength (for example in the case of reconstruction of a femur or metatarsus), the use of a bone substitute comprising a core of any one of the typologies described above and a silicon carbide shell is preferable. In this case, it is preferable to coat the shell with a bioactive layer of collagen mineralized with biomimetic HA or of biomimetic HA alone.

In one embodiment, the bone substitute comprises a core of collagen mineralized with HA partially substituted with ions relevant for the stimulation of bone regeneration processes (biomimetic HA), and a silicon carbide shell.

In another embodiment the bone substitute comprises a biphasic HA/beta-TCP mixture core and an SiC shell.

In another embodiment, the bone substitute comprises a core consisting of collagen mineralized with biomimetic HA and a shell of biomimetic HA or of biphasic HA/beta-TCP mixture.

In the case in which the shell consists of SiC, it is preferable to coat it with a layer of bioactive material, such as collagen mineralized with biomimetic HA, or biomimetic HA, preferably obtained with the method of immersion in SBF. The bone substitute of the invention can be prepared in any desired shape, which can vary according to the specific application for which it is being employed. FIG. 1 illustrates a preferred embodiment of the invention, in which the core has a solid cylinder shape, whereas the shell is a cylinder having a hollow portion therein of a shape corresponding to the cylinder of the core, and of such dimensions as to accommodate the core itself.

The shell is prepared according to the methods described herein below in a hollow cylindrical shape suitable for accommodating the core, which, in turn, can be prepared as a solid cylinder that is inserted in the cavity of the shell. Alternatively, the core can be inserted inside the cylindrical cavity of the shell in gel form and lyophilized later for perfect filling of the cavity. Alternatively, the core can be lyophilized and then introduced into the cylindrical cavity of the shell.

The shell of the bone substitute is of a thickness that varies according to the specific application, but in any case, ranging between 1 and 5 mm, preferably between 2 and 4 mm.

The core of the bone substitute is also of a thickness that varies in accordance with the specific application. The thickness of the entire device is made-to-measure based on the bone defect to be corrected. Considering that the thickness of the shell is kept to a minimum (see above), the thickness of the core is defined as a result.

The layer coating the shell may be of a thickness of between 40 and 100 μm, preferably between 50 and 80 μm.

The core and the shell of hydroxyapatite partially substituted with ions relevant for the stimulation of bone regeneration processes, particularly with magnesium, silicon and/or strontium ions, more preferably the carbonate ion, or of a biphasic mixture of partially substituted HA and beta-TCP, can be obtained by means of two different methods: through a multi-step transformation process or through a sol-gel method.

The multi-step transformation process is known in the sector, for example by the publication by Tampieri A, Sprio S, Ruffini A, Celotti G, Lesci I G, Roveri N. *From Wood to Bone: multi-step process to convert wood hierarchical structures into biomimetic hydroxyapatite scaffolds for bone tissue engineering. J Mater Chem* 2009; 19 (28): 4973-4980.

Such process comprises the following steps:
1) Pyrolysis of native wood: a wood having high porosity (for example, rattan or pine) or a wood having reduced porosity (for example, sipo or oak) is heated to a temperature of between 800 and 2000° C., in an inert atmosphere to permit the decomposition and the elimination of all organic substances. From this process, a carbon material is obtained.
2) Carburization: the carbon material is infiltrated with calcium in the vapour state at a temperature of 1500-1700° C. in an inert atmosphere, transforming it into calcium carbide according to the following reaction:

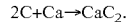

3) Oxidation: the calcium carbide material is completely oxidized at a temperature of 900-1100° C. according to the reaction: $2CaC_2+5O_2 \rightarrow 2CaO+4CO_2$.
4) Carbonation: the calcium oxide material is completely carbonated at temperatures of between 400° C. and 850° C. according to the reaction: $CaO+CO_2 \rightarrow CaCO_3$.
5) Phosphatization: the calcium carbonate material is completely transformed into hydroxyapatite partially substituted with carbonate by means of treatment with a phosphate salt, for example, potassium phosphate.

Substitution with ions other than carbonate can be obtained by introducing suitable soluble salts containing the ions of interest listed above, into the reaction environment of the phosphatization process.

The multi-step method of preparation can optionally also comprise a further step consisting of thermal treatment, in which the hydroxyapatite partially substituted with carbonate ions is partially transformed into β-tricalcium phosphate. In this manner, a biphasic mixture of partially substituted hydroxyapatite and beta-TCP is formed. Such composition is particularly preferred for both the core and the shell, in that it has better bioactivity and bioresorbability, with respect to substituted hydroxyapatite alone, as well as superior mechanical strength properties. Preferably, the thermal treatment is carried out within a temperature range of 700-900° C., preferably in a $CO_2$ atmosphere.

As an alternative to the multi-step transformation method, the biomimetic hydroxyapatite shell and core can be obtained by means of a sol-gel method. A wood having high porosity (for example, rattan or pine) or a wood having reduced porosity (for example, sipo or oak) is infiltrated with a precursor containing phosphite (or phosphate) and/or nitrates. Following infiltration, a gel is prepared at a temperature of between 100 and 150° C.; then this is followed by pyrolization and calcination to eliminate the entire organic part, leaving a porous ceramic material mimicking the structure of the original wood.

To obtain substituted hydroxyapatite, the substitution ions listed above are dispersed in the initial solution by means of the use of soluble salts.

In the case of the sol-gel production method, a thermal treatment method aimed at forming the biphasic mixture of partially substituted HA and beta-TCP is not foreseen. Such mixture can be obtained only with the multi-step method.

The core comprising collagen mineralized with HA partially substituted with ions relevant for the stimulation of bone regeneration processes, preferably carbonate, magnesium, silicon and/or strontium ions, more preferably carbonate and magnesium ions, is obtained using a process known in the sector, for example from the patent publications EP1447104, WO2007045954 and WO2006092718.

The composite material comprises collagen fibres auto-assembled and mineralized with hydroxyapatite substituted with ions relevant for the stimulation of bone regeneration (carbonate, magnesium, silicon, strontium ions). The hybrid composite is reticulated with appropriate products (for example, genipin, glutaraldehyde butanediol diglycidyl ether, etc.) to improve porosity, the microstructure and mechanical properties. Such material is characterized by high porosity and bioactivity determining adequate kinetics of resorption and the formation of well-organized new bone tissue.

The composite material is inserted in the shell cavity in the form of gel and lyophilized later for perfect filling of the cavity.

The silicon carbide shell is obtained by means of a process of infiltration of the pyrolyzed wood with silicon in the liquid state, followed by removal of the excess silicon by means of a suitable chemical attack and final wash to eliminate all traces of residual chemical substances. This material, which is bioinert and well tolerated by the body, preserves the morphology and porosity typical of the original structure of the wood. This permits cell habitation and proliferation, together with sufficient mechanical strength, typical of silicon carbide-based materials, which permits its use in implant sites that are subjected to mechanical loads. The mechanical strength of this device is also determined by its hierarchically organized microstructure, which is typical of substances of natural origin, making it possible to achieve the best and most effective compromise between lightness and mechanical strength, superior to that of other materials with a similar volume of obtained artificially porosity. The hollow cylinder is realized by maintaining a suitable thickness of the external wall with the aim of obtaining the required properties of mechanical strength.

More specifically, the wood precursor having reduced porosity is first subjected to a cycle of pyrolysis at a temperature of up to 1000° C. in an inert (non-oxidizing) atmosphere. During pyrolysis, the organic components of the wood (cellulose, lignin, etc.) are decomposed, leaving a carbon skeleton that reproduces the morphological characteristics of the original wood.

The pyrolyzed sample is then mechanically worked to obtain the desired shape and dimensions; for example, it can be reduced to a hollow cylinder of suitable dimensions.

The pyrolyzed sample is then infiltrated with silicon in the liquid state and under vacuum, so as to permit penetration of the silicon in the porosities and its reaction with the carbon to form silicon carbide according to the reaction:

$$C\ (s) + Si\ (l) \rightarrow SiC\ (s)$$

The transformation into silicon carbide takes place at a final temperature of between 1300 and 1600° C.

The resulting material has residual metallic silicon in the porosities. For the purpose of eliminating it, the sample is subjected to chemical attack with strong acids, such as hydrofluoric acid and/or nitric acid.

This is followed by an eventual wash step, in which residues of the acids are eliminated. The wash is carried out preferably with a solution of $H_3BO_3$.

A shell made of SiC or other material can be coated with a layer of biomimetic material to improve cellular affinity and promote osteointegration. The biomimetic coating can be carried out by means of two processes: electrodeposition of mineralized collagen and deposition of a layer of HA, preferably by immersion in simulated body fluid (SBF).

In electrodeposition, a dual electrode cell is employed, one electrode being a thin sheet of metal, preferably of platinum, and the other, the shell to be coated.

The electrodeposition process takes place preferably at a predetermined constant current and with a number of coating stages that vary according to the microstructure and thickness that one wishes to obtain.

The liquid in which the electrodeposition process takes place comprises a mixture of two solutions, the sources of calcium and phosphorus, respectively, and a collagen suspension.

Under the conditions cited hereinabove, a uniform film of mineralized collagen forms on the surface of the shell, the microstructure and thickness of which depend upon the parameters utilized.

As an alternative to the electrodeposition method, in the event that one wishes to realize a layer in substituted HA, the layer of biomimetic material is realized by means of crystallization of a layer of HA following immersion in simulated body fluid (SBF), containing ions relevant for the promotion of bone regeneration processes (magnesium, silicon ions, etc.).

As a preliminary step, the shell is subjected to attack with a strong acid, preferably with a solution of nitric acid and hydrochloric acid. The shell is then immersed in a solution of $Ca^{2+}$ ions that bind to the surface of the shell. The subsequent immersion in enriched SBF permits the formation of a continuous layer of ionically substituted HA.

The bone substitute of the invention has bioactivity and bioresorbability characteristics combined with mechanical strength characteristics that make it particularly suited for the substitution and regeneration of portions of bone subjected to mechanical loads, for example for the long bones of the leg and arm (for example, the tibia, femur, metatarsus, humerus, radius, etc.)

EXAMPLES

Preparation of a Core of Hydroxyapatite Partially Substituted with Carbonate Ions Multi-Step Method of Transformation:
1) Pyrolysis of Native Wood The rattan wood is dried in a heater at 70° C. for 24 hours and then thermally heated up to 1000° C. in an inert atmosphere to permit the decomposition and the elimination of all organic substances. From this process, a carbon material is obtained.

2) Carburization

The carbon material is infiltrated with calcium in the vapour state at a temperature of 1500-1650° C. in an inert atmosphere, transforming it into calcium carbide according to the following reaction:

$$2C + Ca \rightarrow CaC_2.$$

3) Oxidation

The calcium carbide material is completely oxidized in a furnace at a temperature of 900-1100° C. for 1 hour according to the reaction:

$$2CaC_2 + 5O_2 \rightarrow 2CaO + 4CO_2.$$

4) Carbonation

The calcium oxide material is completely carbonated in a furnace at temperatures exceeding 750° C. in a $CO_2$ atmosphere or under $CO_2$ pressure or in an autoclave at a temperature of 400° C. with a $CO_2$ pressure of 2.2 MPa for 24 hours, according to the reaction:

$$CaO + CO_2 \rightarrow CaCO_3.$$

5) Phosphatization

The calcium carbonate material is completely transformed into hydroxyapatite partially substituted with carbonate under ambient conditions (T<100° C., 1 atm pressure) or hydrothermal conditions at T=200° C., pressure of 1.2 MPa for 24 hours, according to the following reaction:

$$10CaCO_3 + 6KH_2PO_4 + 2H_2O \rightarrow Ca_{10}(PO_4)_6(OH)_2 + 6KHCO_3 + 4H_2CO_3$$

Such formula is an example, given that different sources of phosphate can be employed.

The device thus obtained exhibits a morphology, porosity and mechanical strength compatible with the characteristics of spongy bone.

Sol-Gel Method:

The core of the bone substitute is also prepared using the sol-gel method. The rattan wood is infiltrated with a precursor containing triethyl phosphite and calcium nitrate tetrahydrate in a hydroalcoholic solution (water/ethanol). The molar ratio of water to phosphorus is kept equal to 8 to achieve complete hydrolysis and a ratio of Ca to P equal to 1.67 (that of HA). The solution is left to age for 2 hours at 60° C. until it becomes clear.

The native wood is first purified of the resins having low molecular weight by means of extraction with a Soxhlet apparatus with a mixture of toluol and ethanol (2:1) for 17 hours. Then the samples are dried at 105° C. for 24 hours before performing a second extraction using ethanol for 19 hours.

Following this, the samples are kept in boiling distilled water for several hours and dried at 105° C. for 24 hours.

Infiltration is carried out under vacuum in a beaker containing the sol; following infiltration, the samples are left to dry for several hours at 80° C. to permit formation of the gel. The infiltration process can be repeated to increase the amount of HA.

The samples are then pyrolyzed at 800° C. for 1 h in a nitrogen atmosphere. Lastly, the carbon matrix is removed by sintering at 1300° C.

Such transformation process makes it possible to obtain a biomorphic hydroxyapatite, that is, the transformation of a wood structure into a hydroxyapatite structure that also maintains the original morphology of the wood.

Preparation of a Silicon Carbide Shell

An SiC shell can be obtained according to the processes indicated in the patent publications P200102278 and PCT/ES02/00483.

The sipo wood is first subjected to a cycle of pyrolysis that involves:
1) drying the wood at 75° C. for 24 h and at 120° C. for 24 h;
2) heating up to 1000° C. in an inert (non-oxidizing) atmosphere for a period of 30 minutes, during which the organic components of the wood (cellulose, lignin, etc.) are decomposed, leaving a carbon skeleton that reproduces the morphological characteristics of the original wood.

The pyrolyzed sample is then mechanically worked to obtain the desired shape and dimensions; in this case, it is reduced to a hollow cylinder of suitable dimensions.

The pyrolyzed sample is then infiltrated with silicon in the liquid state and under vacuum, so as to permit penetration of the silicon in the porosities and its reaction with the carbon to form silicon carbide according to the reaction:

$$C\,(s) + Si\,(l) \rightarrow SiC\,(s)$$

The conditions required to achieve the SiC material are: heating 5° C./min and final temperature of 1550° C. maintained for 30 minutes.

The resulting material has residual metallic silicon in the porosities. For the purpose of eliminating it, the sample is subjected to chemical attack according to the following outline of reactions:

$$3Si + 4HNO_3 \rightarrow 3SiO_2 + 4NO + 4H_2O \quad (1)$$

$$3SiO_2 + 12HF \rightarrow 3SiF_4 + 6H_2O \quad (2)$$

$$3Si + 12HF + 4HNO_3 \rightarrow 3SiF_4 + 4NO + 8H_2O \quad (3)$$

The washing process is based on the use of boron hydroxide and permits the elimination of the residues of hydrofluoric acid by means of conversion into a soluble species:

$$B(OH)_3 + 4HF \rightarrow H_3O^+ + BF_4^- + 2H_2O$$

Figure 3:
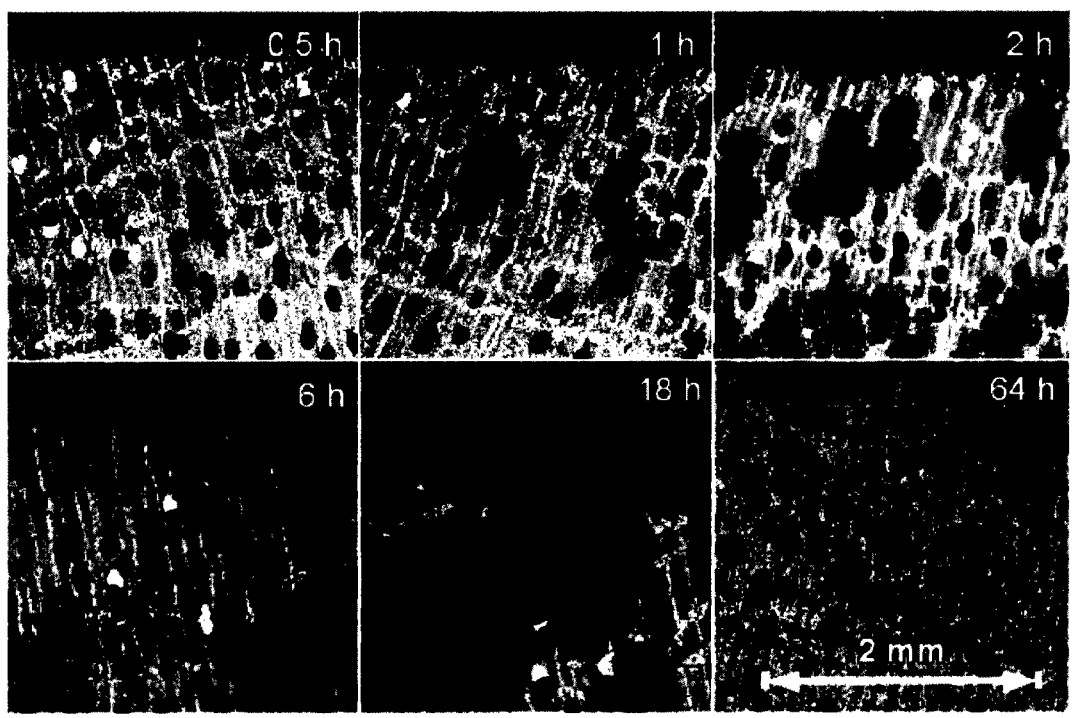
FIG. 3 shows photographs recorded over time of the SiC (silicon carbide) microstructure following removal of excess silicon.

FIG. 3 shows the microstructure of SiC following removal of excess silicon. This image shows how the acid attack gradually frees the porosities of the presence of residual metallic silicon.

Figure 4:
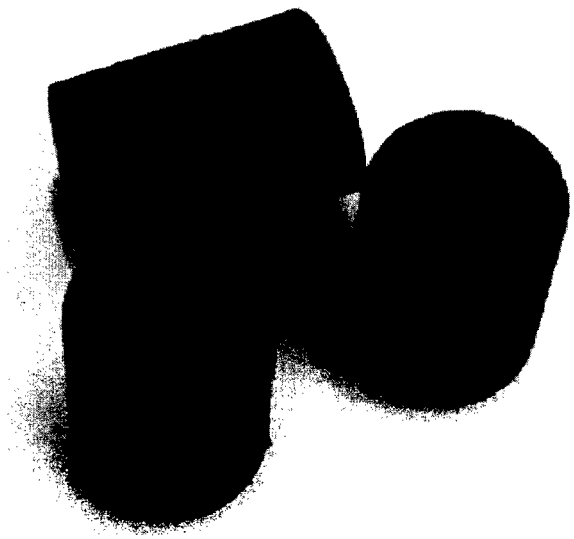
FIG. 4 is a photograph of the shell in SiC according to an embodiment of the invention in which the shell has a hollow cylindrical shape.

FIG. 4 is a photograph of the SiC shell obtained with the described method and that has been given a hollow cylindrical shape.

FIG. 5 shows the compression strength values of the SiC samples obtained with the method.

Preparation of the Hybrid Composite (Collagen Fibres Mineralized with HA Substituted with Carbonate and Magnesium Ions) as the Core.

A calcium hydroxide suspension (1.47 g in 300 cc of water) also containing other ions of interest (utilizing suitable soluble salts of magnesium, silicon, strontium, etc.) is added with an orthophosphoric acid solution (1.17 g in 200 cc of water) charged with 50 g of a suspension of collagen in acetic acid at 1%, at 25° C. The nucleation of the apatite phase on collagen takes place at a pH of 9-12 and preferably at 35° C.

The reticulating agent (for example 1,4-butanediol diglycidyl ether) is added by immersion of the composite in a 2.5 mm of agent for 48 hours. Generally, the achievement of specific ratios of reticulating agent to composite is desired (in this case 1% in weight). After this treatment, the construct is washed, filtered and inserted in the cavity of the SiC cylinder in the form of gel and lyophilized later for perfect filling of the cavity. Alternatively, the construct can be lyophilized and then introduced into the cavity of the SiC cylinder.

Preparation of an SiC Shell Coated with Bioactive Film.

Biomimetic coating is carried out by two methods: electrodeposition of mineralized collagen and deposition of a layer of biomimetic HA, by immersion in simulated body fluid (SBF).

Electrodeposition Method

Coating is achieved by electrodeposition in a dual electrode cell, one electrode being a thin sheet of platinum, and the other, the SiC shell.

The process takes place at a predetermined constant temperature (for example ambient T), within a predetermined period of time (for example 15 minutes), at a predetermined constant current (for example 34 mA) and with a number of coating stages that differs according to the microstructure and thickness that one wishes to obtain.

The liquid in which the electrodeposition process takes place consists of a mixture of two solutions, the sources of calcium (for example, calcium nitrate, 42 mM) and phosphorus (for example, monobasic ammonium phosphate, 25 mM), respectively, plus a collagen suspension prepared starting from equine Achilles tendons, by means of the method developed by Opocrin S.p.A (WO 0209790).

Under the conditions cited above, a uniform film of mineralized collagen forms on the surface of the SiC, the microstructure and thickness of which depend upon the parameters utilized.

Figure 6:
FIG. 6 is a photograph of an SiC shell before (left) and after (right) deposition of a hydroxyapatite (HA)/collagen composite coating.

FIG. 6 shows the cylinder-shaped shell before and after coating with the film of collagen mineralized with hydroxyapatite according to the described method.

Figure 7:
FIG. 7 shows a TEM image witnessing the nucleation of nanometric HA crystals on fibres of collagen by electrophoresis deposition.

FIG. 7 shows the presence of nanometric HA crystals on fibres of collagen, as obtained with the described method.

SBF Method

The functionalization of the surface of the cylinders in BioSiC is achieved by means of the crystallization of a layer of HA following immersion in simulated body fluid (SBF), containing ions relevant for the promotion of the processes of bone regeneration (magnesium, silicon, etc.).

As a preliminary step, the surface of the cylinders is subjected to acid attack by means of an $HNO_3/HCl$ solution, which results in the formation of $COO^-$ ions.

The cylinder is then immersed in a solution of calcium chloride so that the previously activated surface can bind the $Ca^{2+}$ ions present in the solution. The subsequent immersion in enriched SBF permits the formation of a continuous layer of ionically substituted HA.

Figure 8:
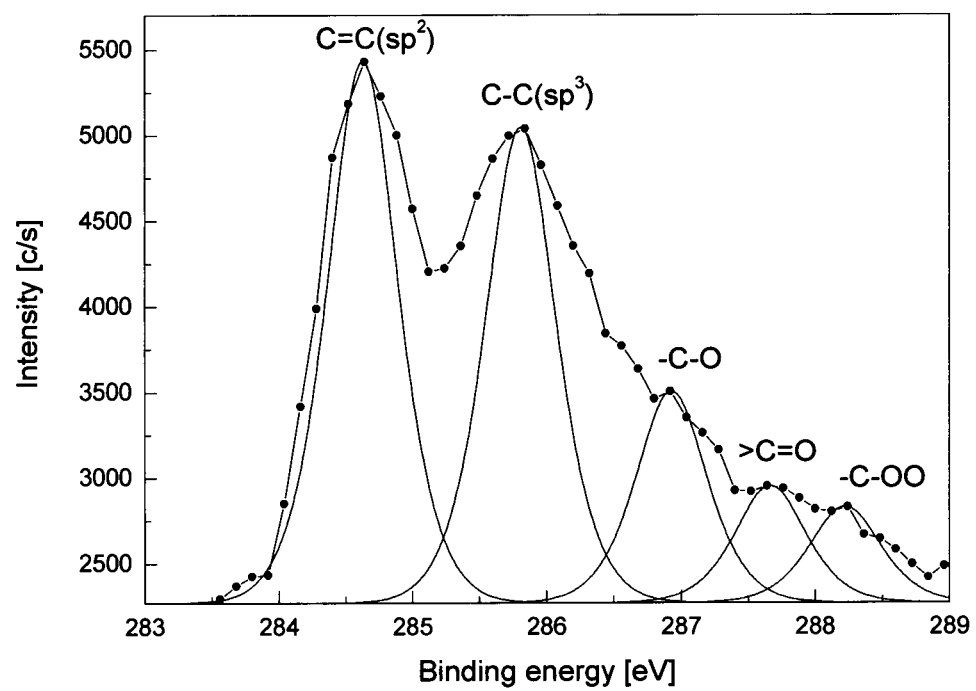
FIG. 8 shows the results of the XPS spectroscopy of the surfaces of SiC shells, in which the formation of $COO^-$ groups following acid attack is highlighted; the $COO^-$ groups serve to coordinate the calcium ions during the coating process by means of immersion in simulated body fluid (SBF)

FIG. 8 shows the results of the XPS spectroscopy of the surfaces of SiC shells, in which the formation of $COO^-$ groups following acid attack is highlighted; the $COO^-$ groups serve to coordinate the calcium ions during the coating process by means of immersion in SBF.

Figure 9:
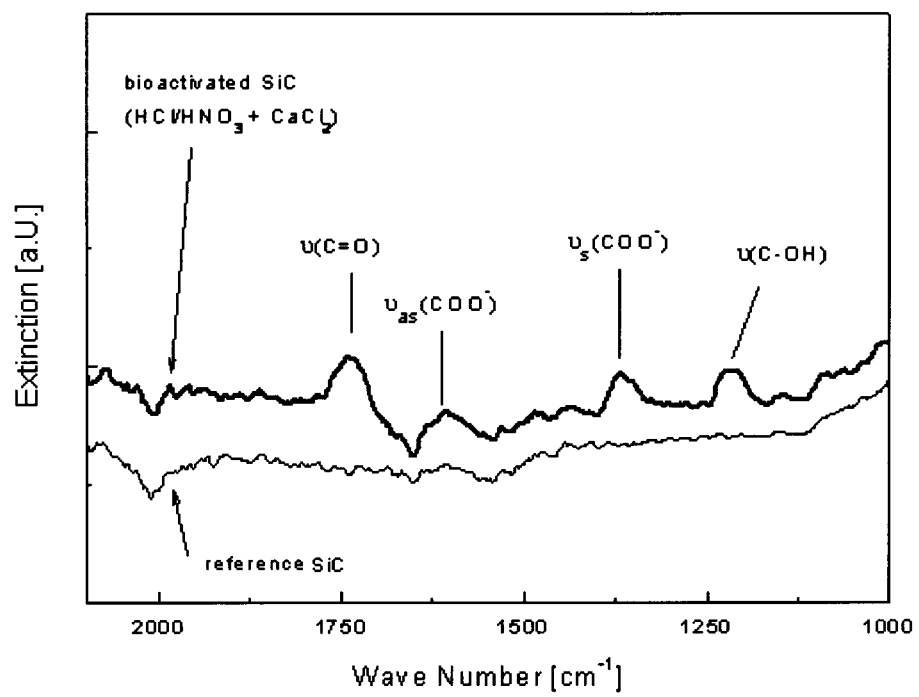
FIG. 9 shows the results of the FTIR spectroscopy of the surface of SiC shells, in which the formation of $COO^-$ groups following acid attack is highlighted; the $COO^-$ groups serve to coordinate the calcium ions during the coating process by means of immersion in SBF.

FIG. 9 shows the results of the FTIR spectroscopy of the surface of SiC shells, in which the formation of COO groups following acid attack is highlighted; the COO groups serve to coordinate the calcium ions during the coating process by means of immersion in SBF.

Figure 10:
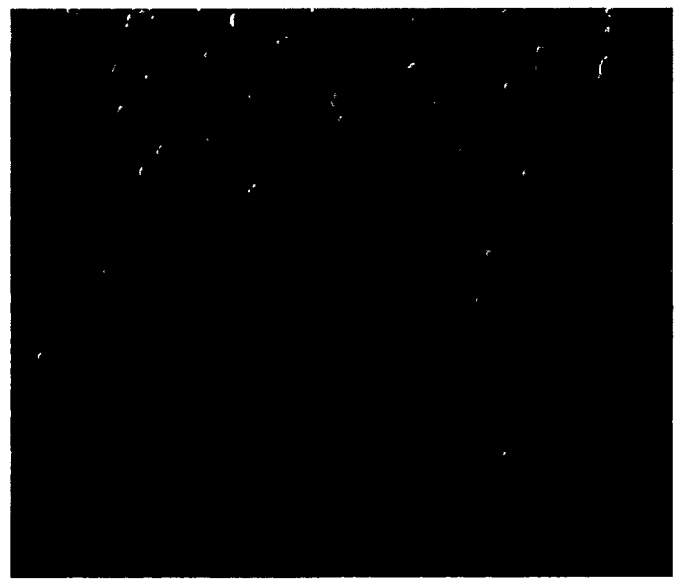
FIG. 10 is a photograph of the microstructure of an SiC shell coated with a layer of biomimetic hydroxyapatite by means of immersion in SBF (after the surface had been subjected to acid attack as specified in the two preceding figures)

FIG. 10 shows the microstructure of the SiC coated with the bioactive film of biomimetic hydroxyapatite obtained from SBF.

FIG. 11 shows the assembled bone substitute of the invention; an HA/collagen core and an SiC shell are observable in photograph A, whereas a substituted HA core and an SiC shell are observable in photograph B.

Biomorphic bone substitutes exhibit an orientated and anisotropic morphology and thus their mechanical strength changes considerably in the two directions. For example, the SiC shells derived from red oak and sipo have a compression strength of 150 and 50 MPa, in the longitudinal and transversal directions, respectively. The biomimetic HA scaffolds derived from rattan, for example, show a compression strength of 4-5 and circa 1 MPa, respectively.

Figure 12:
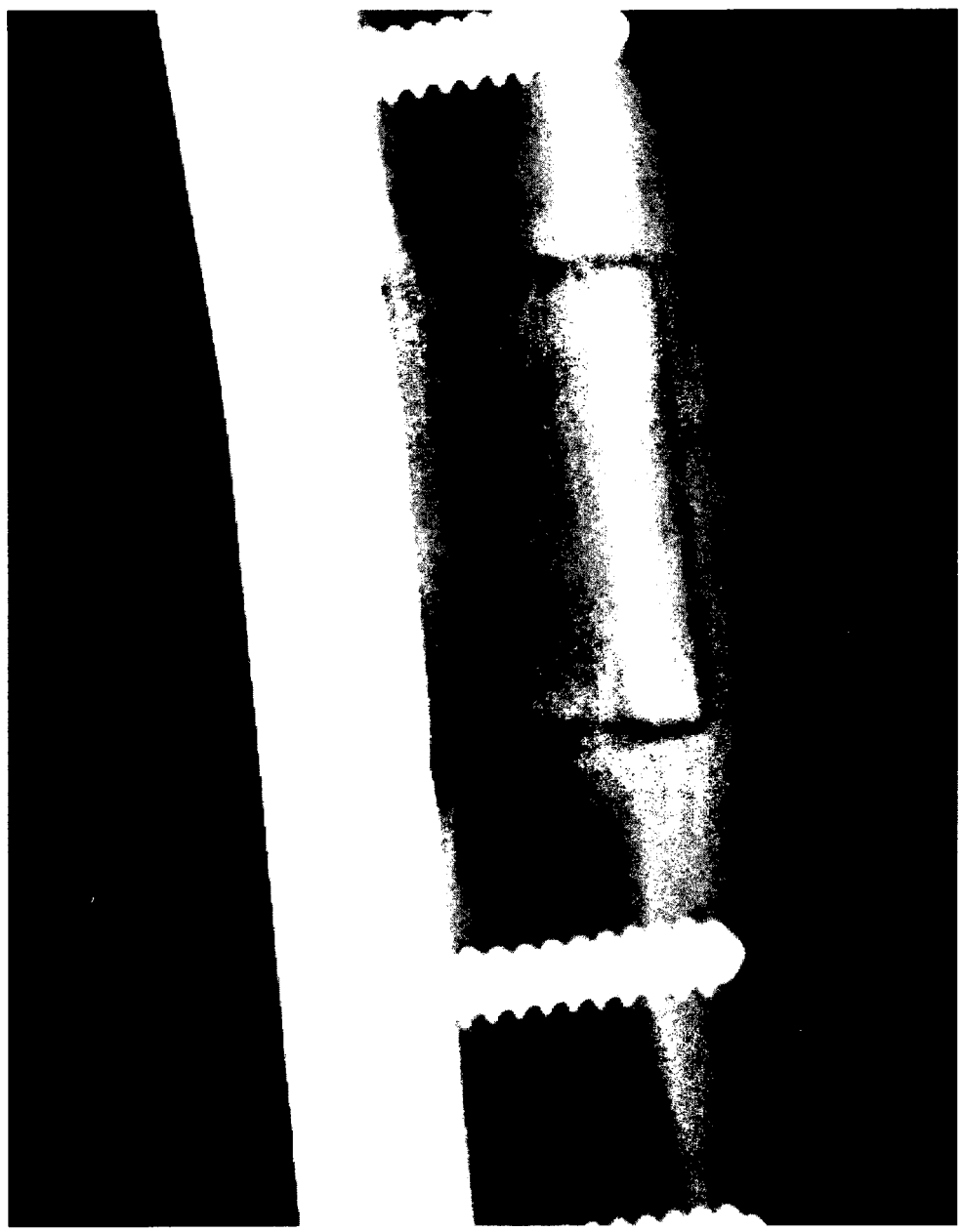
FIG. 12 shows an X-ray of a biomorphic implant in a critical defect in a sheep metatarsal bone, highlighting the osteointegration of the SiC shell.
Figure 13:
FIG. 13 shows the histological sections of a biomorphic implant in a critical defect in a sheep metatarsal bone, highlighting the osteointegration of the SiC shell.
Figure 14:
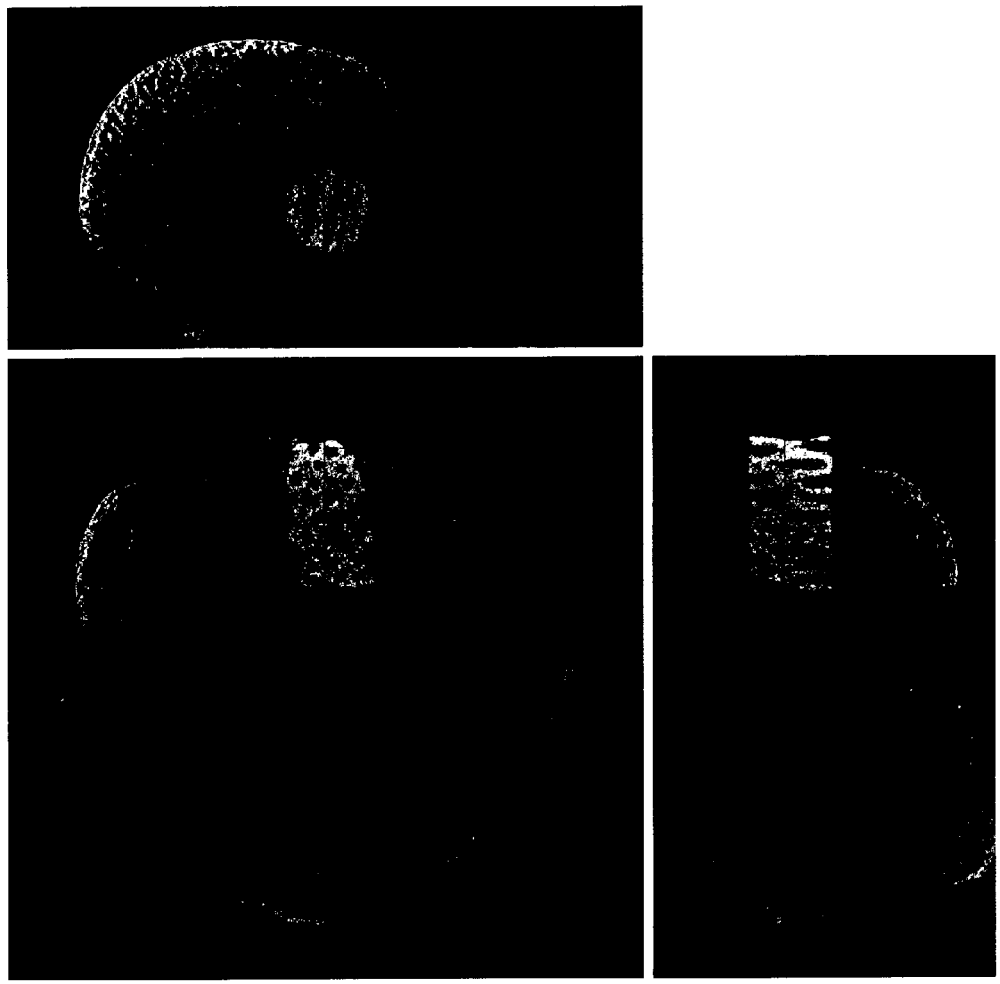
FIG. 14 shows the Micro-CT of a biomorphic HA implant obtained from rattan wood in trabecular bone in the distal area of a rabbit femur, highlighting the perfect osteointegration of the scaffold in the surrounding bone.

The images from in vivo tests carried out on a sheep (FIGS. 12-13) and rabbit (FIG. 14) show, respectively, the osteointegration of the SiC shell derived from sipo and the osteointegration of the biomimetic HA core obtained with the multistep method (FIG. 14).

The invention claimed is:

1. A bone substitute comprising a core and a shell, the shell covering at least part of an exterior surface of the core, the core comprising one or more of hydroxyapatite and substituted hydroxyapatite, the core having a first porosity, the core having a pore structure and being derived from a first wood in such a way that the pore structure of the core corresponds to a pore structure of the first wood, the first wood being selected from the group consisting of rattan, pine, abachi and balsa wood, the shell comprising one or more of hydroxyapatite and substituted hydroxyapatite, the shell having a pore structure and being derived from a second wood in such a way that the pore structure of the shell corresponds to a pore structure of the second wood, the second wood having a porosity which is less than the porosity of the first wood, the second wood being selected from the group consisting of sipo, oak, rosewood and kempas, the shell being coated with a layer comprising collagen mineralized with hydroxyapatite.

2. The bone substitute according to claim 1, wherein said first wood has a total porosity of between 60% and 95%.

3. The bone substitute according to claim 1, wherein said second wood has a porosity of between 30% and 50%.

4. The bone substitute according to claim 1, wherein said core comprises substituted hydroxyapatite, wherein said substituted hydroxyapatite comprises hydroxyapatite partially substituted with ions selected from the group consisting of carbonate, magnesium, silicon and strontium ions and mixtures thereof.

5. The bone substitute according to claim 1, wherein said shell comprises substituted hydroxyapatite, wherein said substituted hydroxyapatite comprises hydroxyapatite partially substituted with ions selected from the group consisting of carbonate, magnesium, silicon and strontium ions and mixtures thereof.

6. The bone substitute according to claim 1, wherein said layer coating the shell further comprises hydroxyapatite partially substituted with ions selected from the group consisting of carbonate, magnesium, silicon and strontium ions and mixtures thereof.

7. The bone substitute according to claim 1, wherein said shell has a thickness of between 1 and 5 mm.

8. The bone substitute according to claim 1, wherein said core has a solid cylinder shape, and wherein said shell is a cylinder having a hollow portion therein of a shape corresponding to the cylinder shape of the core and of such dimensions as to accommodate the core.

9. The bone substitute according to claim 1, wherein said second wood has a porosity of between 20% and 60%.

10. The bone substitute according to claim 1, wherein said first wood has a porosity of between 65% and 85%.

11. The bone substitute according to claim 1, wherein said core comprises a biphasic mixture comprising ionically substituted hydroxyapatite and β-tricalcium phosphate (beta-TCP; $Ca_3(PO_4)_2$).

12. The bone substitute according to claim 1, wherein said shell comprises a biophasic mixture comprising ionically substituted hydroxyapatite and β-tricalcium phosphate (beta-TCP; $Ca_3(PO_4)_2$).

13. The bone substitute according to claim 1, wherein said layer has a thickness of between 40 and 100 μm.

14. A bone substitute comprising a core and a shell, the shell covering at least part of an exterior surface of the core, the core comprising one or more of hydroxyapatite and substituted hydroxyapatite, the shell comprising one or more of hydroxyapatite and substituted hydroxyapatite;
  the core being produced (A) by a process comprising the following steps:
    (a) pyrolyzing a first wood to yield a carbon material, the first wood being selected from the group consisting of rattan, pine, abachi and balsa wood; and
    (b) thereafter transforming the carbon material to yield one or more of hydroxyapatite and substitute hydroxyapatite;
  OR
  (B) by a process comprising the following steps:
    (a) treating the first wood and then infiltrating the treated first wood with a precursor to yield a first precursor material;
    (b) pyrolyzing the first precursor material to yield a second precursor material; and
    (c) thereafter transforming the second precursor material to yield one or more of hydroxyapatite and substituted hydroxyapatite;
  the shell being produced (A) by a process comprising the following steps:
    (a) pyrolyzing a second wood to yield a carbon material, the second wood being selected from the group consisting of sipo, oak, rosewood and kempas; and
    (b) thereafter transforming the carbon material to yield one or more of hydroxyapatite and substitute hydroxyapatite;
  OR
  (B) by a process comprising the following steps:
    (a) treating the second wood and then infiltrating the treated second wood with a precursor to yield a first precursor material;
    (b) pyrolyzing the first precursor material to yield a second precursor material; and
    (c) thereafter transforming the second precursor material to yield one or more of hydroxyapatite and substituted hydroxyapatite;
  wherein the second wood has a porosity which is less than the porosity of the first wood, the core having a pore structure which corresponds to a pore structure of the first wood, the shell having a pore structure which corresponds to a pore structure of the second wood, the shell being coated with a layer comprising collagen mineralized with hydroxyapatite.

15. A method of substituting or regenerating a bone or a bone portion, comprising a step of implanting a bone substitute according to claim 1.

16. The method according to claim 15, wherein said bone or bone portion is a bone or bone portion which is load-bearing.

17. The method according to claim 16, wherein said bone or bone portion is a long bone of the leg or arm.

* * * * *